United States Patent
Atwood

(10) Patent No.: US 9,908,874 B2
(45) Date of Patent: Mar. 6, 2018

(54) SEPARATION METHOD FOR ACTIVE PHARMACEUTICAL INGREDIENTS (APIS) FROM EXCIPIENTS IN PHARMACEUTICAL FORMULATIONS

(71) Applicant: Jerry L. Atwood, Columbia, MO (US)

(72) Inventor: Jerry L. Atwood, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 0 days.

(21) Appl. No.: 15/137,868

(22) Filed: Apr. 25, 2016

(65) Prior Publication Data

US 2016/0340350 A1 Nov. 24, 2016

Related U.S. Application Data

(60) Provisional application No. 62/152,357, filed on Apr. 24, 2015.

(51) Int. Cl.
  *C07D 417/12* (2006.01)
  *C07D 211/22* (2006.01)

(52) U.S. Cl.
  CPC .......... *C07D 417/12* (2013.01); *C07D 211/22* (2013.01)

(58) Field of Classification Search
  CPC .............................. C07D 417/12; B03B 5/32
  See application file for complete search history.

(56) References Cited

PUBLICATIONS

Atwood et al., "4-Bromo-2,3-dicarbomethoxy-2-cyclohepten-1-one", Acta Crystallographica, 1974, pp. 2066-2068, vol. B 30, Part 8.
Tian et al., "A New Strategy of Transforming Pharmaceutical Crystal Forms", Journal of the American Chemical Society, 2011, pp. 1399-1404, vol. 133.

*Primary Examiner* — Paul V Ward
(74) *Attorney, Agent, or Firm* — Polsinelli PC

(57) ABSTRACT

The present invention provides a method for physically separating the active pharmaceutical ingredient (API) from the excipients in a pharmaceutical formulation before the API is fully characterized by standard techniques. The presently disclosed method is based on making use of the difference in density of the API and that of the excipients. In the method, the API is not dissolved, nor is the crystal form of the API changed.

19 Claims, 10 Drawing Sheets

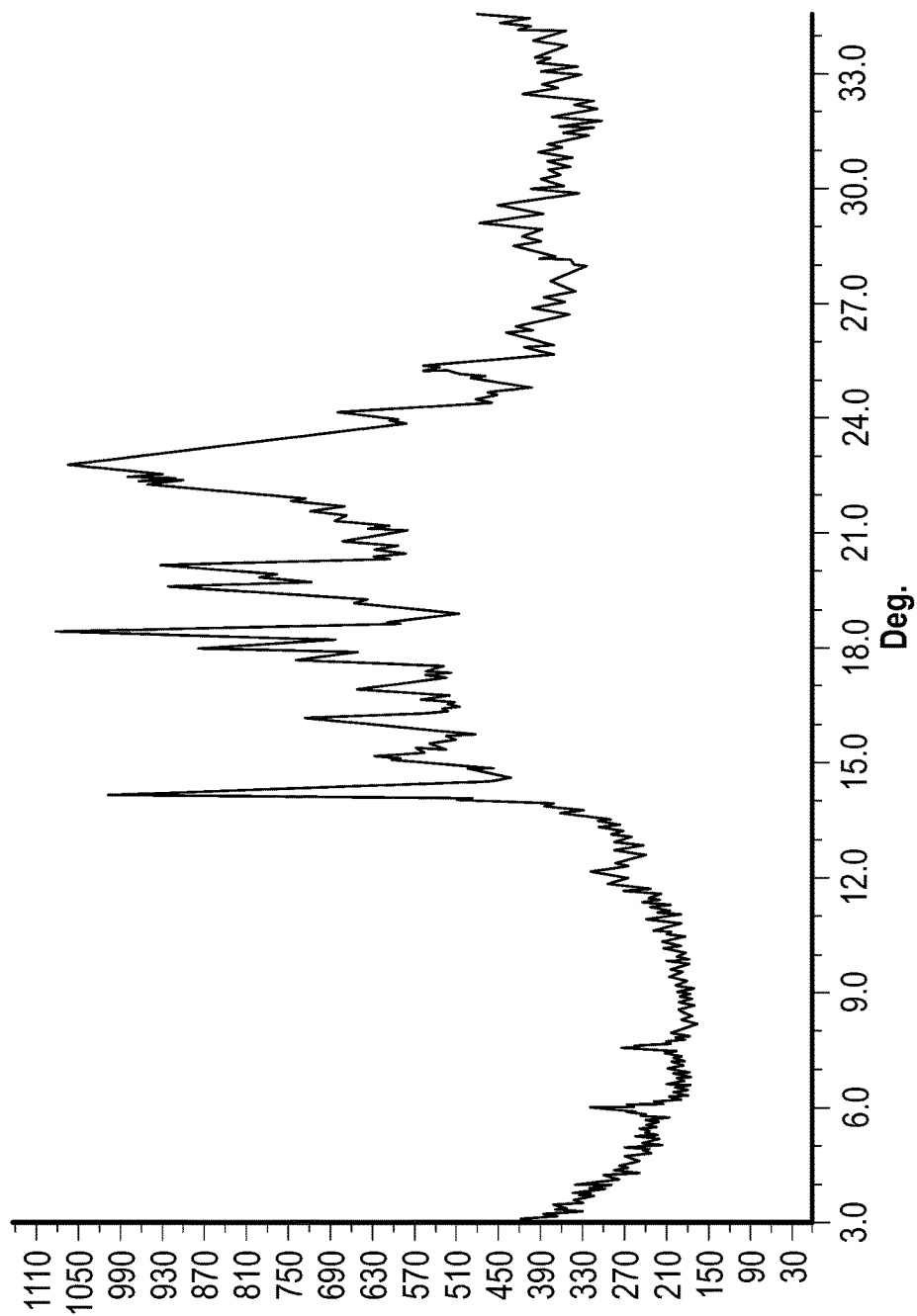

SEPARATION METHOD FOR ACTIVE PHARMACEUTICAL INGREDIENTS (APIS) FROM EXCIPIENTS IN PHARMACEUTICAL FORMULATIONS

CROSS-REFERENCE TO RELATED APPLICATIONS

This application claims priority to U.S. Provisional Application No. 62/152,357 filed Apr. 24, 2015, the contents of which are incorporated by reference.

GRANT STATEMENT

None.

FIELD

The present teachings relate to pharmaceutical formulations, and more particularly to a method of separating active pharmaceutical ingredients from excipients in pharmaceutical formulations.

BACKGROUND

The analysis of formulated drug products has been of increasing importance over the last several years. The potential for decomposition of the active pharmaceutical ingredient (API) has always placed emphasis on the analysis of the compound itself. This has routinely been accomplished by techniques such as HPLC. However, HPLC is powerless to speak to the crystal form of the API. For crystal form analysis, scientists have placed emphasis on techniques such as XRPD, infrared and Raman spectroscopy, and solid-state NMR. For the characterization of the API, these 'fingerprint' techniques are excellent individually, and even more powerful in combination. However, the API is often a minor component by weight in a tablet or other formulation. The presence of the excipients can interfere with the analysis of crystal forms.

In the evaluation of crystal form, for best results one must separate the excipients from the API in a pharmaceutical formulation. Dissolution is not an option, since the crystal form is lost in solution. The API has frequently been formulated as a salt if the molecule itself is not readily water-soluble. Most excipients are also water-soluble.

The crystallography of five decades past was not based on a high production of single crystal X-ray structures. Indeed, by the early 1970's a rule of thumb was that a crystallographer with a modern (as of 1970) four-circle X-ray diffractometer and a moderate size research group should strive to do five or six structures per year. Times have changed. Today, moderate sized research groups commonly do more than ten X-ray crystal structures per week. Computer and diffractometer power have consumed much of the art of the crystallography of the 1960's.

In the 1960's and 1970's, the measurement of the density of single crystals was, depending on the journal, mandatory for publication. The density measurement was performed by placing the crystal in a fluid medium in which the crystal was not soluble. The density of the fluid was then adjusted (by adding solute or other miscible fluids) so that the crystal under analysis would float half way up in the column of fluid. At that point, the density of the crystal was equal to the density of the fluid medium.

Therefore, there is a need to provide a new and improved method for physically separating an API from excipients in a pharmaceutical formulation.

SUMMARY

The present disclosure provides a new and improved method for physically separating one or more APIs from excipients in a pharmaceutical formulation, before fully characterizing the API by standard techniques. The presently disclosed method is based on a density separation method that includes the use of liquid separation media, having selected densities, in which the API is insoluble. The density separation method may also be employed for the determination of the melting point or of the state of hydration of the API.

BRIEF DESCRIPTION OF THE DRAWINGS

The drawings described herein are for illustration purposes only and are not intended to limit the scope of the present teachings in any way.

FIG. 1A shows the XRPD pattern of the crushed and lightly ground tablets (Allegra Allergy WalMart Brand).

DETAILED DESCRIPTION

Figure 1B:
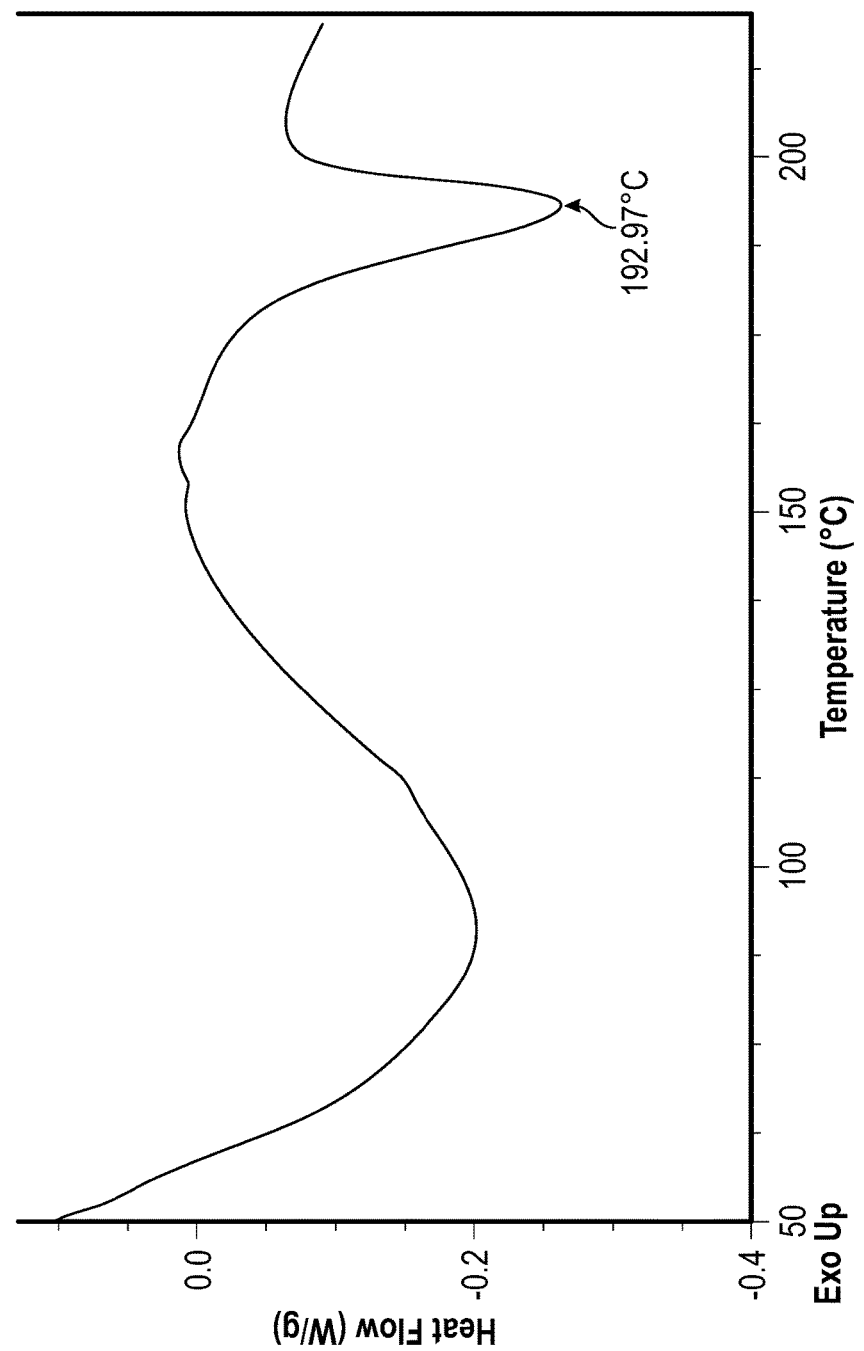
FIG. 1B shows the DSC thermogram of the crushed and lightly ground Allegra tablets.

The present disclosure provides a method of physically separating an active pharmaceutical ingredient (API) from a pharmaceutical formulation that includes an API and excipients, so that the API may be fully characterized by standard techniques. The method uses liquid separation media having selected densities which provide for the physical separation of APIs from excipients in a pharmaceutical formulation. Most APIs have densities in the range of 1.1 g/cm$^3$ to 1.5 g/cm$^3$, with even more APIs in the narrower 1.2 g/cm$^3$ to 1.4 g/cm$^3$ range. In contrast, common crystalline excipients generally fall into two ranges, those with densities over 1.5 g/cm$^3$ and those with densities less than 1.15 g/cm$^3$. The liquid separation media are additionally selected so that the API is insoluble in the liquid separation media so that the API is not dissolved, nor is the solid form of the API changed during the separation method.

The liquid separation media may be generated by mixing two miscible liquids, one less dense and one denser, so that liquid separation media having a wide range of precisely selected densities may be produced. Mixtures of halocarbons and hydrocarbons work well, and in examples described herein, the mixture of iodobenzene and hexane (or toluene or cyclohexane) has been found to work well. With densities of 1.823 g/cm$^3$ for iodobenzene, 0.865 g/cm$^3$ for toluene, 0.778 g/cm$^3$ for cyclohexane, and 0.655 g/cm$^3$ for hexane, most pharmaceutical formulations are amenable to mixtures of iodobenzene and toluene, cyclohexane, or hexane.

According to at least one aspect of the present disclosure, the method includes providing the pharmaceutical formulation in a powdered form that includes a mixture of API particulates and excipient particulates. The method may further include generating a first liquid separation medium in which the API is insoluble. The generated first liquid separation medium may have a selected density greater than the density of the API particulates, but less than the density of at least a portion of excipient particulates. The powdered form of the formulation, including API particulates and excipient particulates, may be introduced to a vessel containing the first liquid separation medium. The vessel containing the first liquid separation medium and the particulates may then be centrifuged so that the particulates having a density less than the density of the first liquid separation medium are floated to form a first floated fraction while the particulates having a density greater than the first liquid separation medium forms a first pellet fraction at the bottom of the vessel. The first floated fraction, including at least a portion of the API particulates, may be removed from the vessel.

According to at least one aspect of the present disclosure, the method further includes generating a second liquid separation medium having a selected density that is less than the density of the API particulates and greater than the density of at least a portion of the excipient particulates. As is the case for the first liquid separation medium, the second liquid separation medium is further selected such that the API is insoluble in the second liquid separation medium. The first floated fraction, including at least a portion of the API particulates, may be introduced to a vessel containing the second liquid separation medium. The vessel containing the first floated fraction and the second liquid separation medium may be centrifuged so that the particulates having a density less than the density of the second liquid separation medium are floated to form a second floated fraction and the particulates having a density greater than the second liquid separation medium forms a second pellet fraction at the bottom of the vessel. The second pellet fraction, including at least a portion of the API particulates, may be removed from the vessel.

The presently disclosed method may further include sequential treatment of the removed floated fractions or pellet fractions, containing API particulates, with additional liquid separation media to achieve greater separation of API particulates from excipient particulates. For example, following removal of the first floated fraction, the first floated fraction may be treated with one or more additional liquid separation media having a selected density that is greater than the density of the API particulates. Further, the first floated fraction may be sequentially treated with one or more additional liquid separation media having decreasing selected densities that are still greater than the density of API particulates.

Additionally, in some instances, the presently disclosed method may include only the first liquid separation medium or only the second liquid separation medium. In such cases, separation of the API from excipient particulates having either greater or lesser density than the API particulates may be sufficient to allow for characterization of the API using standard techniques.

Additionally, liquid separation media having selected densities either greater or less than the API may be used in any order without departing from the spirit and scope of the present disclosure. For example, a liquid separation medium having a selected density that is less than that of the API particulates may be used to treat the powdered form of the pharmaceutical formulation prior to the use of a liquid separation medium having a density greater than the API particulates, without departing from the spirit and scope of the present disclosure.

As used herein, the term "pharmaceutical formulation" refers to any tablet, mini-tablet, capsule, or the like that includes one or more APIs and one or more excipients in the form of a solid. As used herein, the term "particulates" refers to any solid particle containing one or more APIs or one or more excipients. As used herein, the term "solid form" refers to any solid state or polymorphic form of an active pharmaceutical ingredient, including, but not limited to, a crystalline form, a semi-crystalline form, an amorphous form, a substantially crystalline form, and a substantially amorphous form. Generally, the solid form of an API may be characterized using standard techniques, such as XRPD, infrared and Raman spectroscopy, solid-state NMR, and DSC.

According to at least one aspect of the present disclosure, the first or second liquid separation media may be generated by mixing two miscible liquids having different densities to produce the first or second liquid separation media having the selected density. In at least some instances, the two miscible liquids may be a halocarbon and a hydrocarbon. In at least some instances, the two miscible liquids may include a first more dense liquid having a density between about 1.6 g/cm$^3$ to about 2.0 g/cm$^3$ and a second less dense liquid having a density between about 0.6 g/cm$^3$ to about 0.9 g/cm$^3$. In at least some instances, the first more dense liquid may be selected from, but not limited to, iodobenzene (1.83 g/cm$^3$), bromopropane (1.70 g/cm$^3$), bromobutane (1.62 g/cm$^3$), 1,4-dibromobenzene (1.84 g/cm$^3$), or 1,3-dibromobenzene (1.95 g/cm$^3$). In at least some instances, the second less dense liquid may be selected from, but not limited to, hexane (0.66 g/cm$^3$), cyclohexane (0.78 g/cm$^3$), toluene (0.87 g/cm$^3$), o-xylene (0.87 g/cm$^3$), pentane (0.63 g/cm$^3$), or heptane (0.68 g/cm$^3$).

According to at least one aspect of the present disclosure, the two miscible liquids used to generate the first or second liquid separation media may be two aqueous solutions having different solutes or solute concentrations, and therefore different densities. In at least some instances, the solute may be a salt. In at least some instances, the salt may be selected from, but not limited to, CsCl, KBr, CsBr, CsI, RbCl, RbBr, RbI, and KI. CsCl has a solubility of 1.86 g/cm$^3$ at 20° C., therefore one milliliter of water saturated with CsCl has a density of about 2.86 g/cm$^3$. KBr has a solubility of 0.68 g/cm$^3$ at 25° C., therefore one milliliter of water saturated with KBr has a density of about 1.68 g/cm$^3$. In at least some instances, the two miscible liquids may include a first more dense liquid in the form of an aqueous solution saturated with CsCl and a second less dense liquid in the form of water, having a density of about 1.0 g/cm$^3$. In at least some instances, the two miscible liquids may include a first more dense liquid in the form of an aqueous solution saturated with KBr and a second less dense liquid in the form of water, having a density of about 1.0 g/cm$^3$.

According to at least one aspect of the present disclosure, generating the first or second liquid separation media may include dissolving a solute in water to produce the first or second liquid separation media having the selected density. In at least some instances, the salt may be selected from, but not limited to, CsCl, KBr, CsBr, CsI, RbCl, RbBr, RbI, and KI.

According to at least one aspect of the present disclosure, the density of the API particulates may be between about 1.1 g/cm$^3$ to about 1.5 g/cm$^3$. In at least some instances, the desnity of the API particulates is between about 1.2 g/cm$^3$ to about 1.4 g/cm$^3$. In at least some instances, the density of the excipient particulates is less than about 1.1 g/cm$^3$ or greater than about 1.5 g/cm$^3$.

The selected density of the first liquid separation medium may be in the range of a lower limit of about 1.1 g/cm$^3$, 1.15 g/cm$^3$, 1.2 g/cm$^3$, 1.25 g/cm$^3$, and 1.3 g/cm$^3$, to an upper limit of about 1.6 g/cm$^3$, 1.55 g/cm$^3$, 1.50 g/cm$^3$, 1.45 g/cm$^3$, 1.40 g/cm$^3$, 1.35 g/cm$^3$, and 1.30 g/cm$^3$, encompassing any value and subset there between. The selected density of the second liquid separation medium may be in the range of a lower limit of about 1.1 g/cm$^3$, 1.15 g/cm$^3$, 1.2 g/cm$^3$, 1.25 g/cm$^3$, and 1.3 g/cm$^3$, to an upper limit of about 1.6 g/cm$^3$, 1.55 g/cm$^3$, 1.50 g/cm$^3$, 1.45 g/cm$^3$, 1.40 g/cm$^3$, 1.35 g/cm$^3$, and 1.30 g/cm$^3$, encompassing any value and subset there between. In at least some instances, the selected density of the first liquid separation medium and the second liquid separation medium is between about 1.1 g/cm$^3$ to about 1.5 g/cm$^3$.

According to at least one aspect of the present disclosure, the method further includes providing the powdered form of the pharmaceutical formulation by applying mechanical energy to the pharmaceutical formulation with sufficient force and duration to generate a powdered form of the pharmaceutical formulation. Mechanical energy may be applied to the pharmaceutical formulation in the form of grinding, crushing, or milling, so long as there is no conversion of the solid form of the API during the application of mechanical energy. In at least some instances, the pharmaceutical formulation may be crushed using a mortar and pestle under normal hand pressure. The intensity of the grinding necessary to generate the powdered form of the pharmaceutical formulation without causing the conversion of the solid form of the API must be determined for each sample or brand of each pharmaceutical formulation.

According to at least one aspect of the present disclosure, the method further includes performing sonication on the vessel containing the first liquid separation medium and the particulates with sufficient force and duration to free the API particulates from the excipient particulates. If the excipients are tightly packed with the API, agitation may be necessary to free the particulates of the API from the excipient particulates. A sonication treatment of the vessel containing particulates and the liquid separation medium works well. Enough sonication must be applied to free the excipient particulates from the particulates of the API, and this variable must be experimentally determined. Note that the API must be stable under exactly the same conditions as those to which the formulation is subjected, including the degree of sonication. The sonication of the vessel may be performed after the particulates have been introduced to the liquid separation medium and before the vessel is centrifuged. In at least some instances, sonication for 5 minutes using a Crest Tru-Sweep 275 HT sonicator may be sufficient to free the excipient particulates from the API particulates.

Depending on the formulation, some excipient particles or crystals may adhere strongly to the API particulates. This has often proved to be case for lactose monohydrate, mannitol and sucrose. If excipients stick to the API, it may be necessary for the density separation method to be applied several times to achieve the desired level of separation. The only limitation is the amount of formulated API available. Each pass through the density separation process requires material.

It is necessary to dry the density separated API from the iodobenzene/hexane liquid. Washing the API with hexane immediately after removing most of the iodobenzene/hexane by centrifugation and decantation, works well. Generally, the API should be washed twice with hexane, with a centrifugation separation after each washing. The residual hexane may then be removed by 10 minutes in a vacuum chamber at 50 torr and room temperature.

According to at least one aspect of the present disclosure, the solid form of the API does not change during the presently disclosed separation method, as determined by standard techniques, such as XRPD. However, one must always test the target API(s) to make sure no solid form conversion occurs using the density separation method. This is best ascertained by utilizing a standard sample of the target API under exactly the same conditions as used to density separate the formulation. As a final check to insure that the solid form of the API has not changed during the presently disclosed separation method, it may be appropriate to compare the density separated API with the initial pharmaceutical formulation by XRPD or some other technique of choice. One should find the peaks due to the API are now relatively prominent compared to those of the excipients.

According to at least one aspect of the present disclosure, the separation method sufficiently separates the excipient particulates from the API particulates to allow for characterization of the solid form of the API by standard techniques, such as XRPD, infrared and Raman spectroscopy, solid-state NMR, and DSC. In at least some instances the presently disclosed separation method provides for sufficient separation of the crystalline excipient particulates to allow for polymorphic characterization of the API. According to at least one aspect of the present disclosure the separation method provides for API characterized by a purity of between about 85% to about 99% by weight.

The API separated from excipients according to the presently disclosed separation method may be tested in any desired manner. This procedure also works very well for the determination of the melting point or of the state of hydration of the API.

The presently disclosed separation method is suitable for separation of an API from pharmaceutical compositions including, but not limited to, those having the brand name Lipitor, Plavix, Nexium, Abilify, Seroquel, Januvia, Reyataz, Niaspan, Vyvanse, Venlafaxine, Zyvox, Treanda, Exelon, Atorvastatin, Onglyza, Norvir, Revlimid, Tarceva, Pristiq, Celebrex, Lyrica, Crestor, Actos, Cymbalta, Oxycontin, Lexapro, Cialis, Levaquin, Dexilant, Aloxi, Invega, Valcyte, Avelox, and Chantix.

All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or equivalently, "from approximately a to b," or, equivalently, "from approximately a-b") disclosed herein is to be understood to set forth every number and range encompassed within the broader range of values. Moreover, the indefinite articles "a" or "an," as used in the claims, are defined herein to mean one or more than one of the element that it introduces.

Example 1

Separation of Fexofenadine HCl from Allegra Allergy 24 Hour Tablets.

The commercial product Allegra Allergy 24 Hour Tablets, obtained from WalMart, according to the label consists of tablets containing 180 mg of fexofenadine HCl with colloidal silicone dioxide, croscarmellose sodium, hypromellose, iron oxide blends, magnesium stearate, microcrystalline cellulose, polyethylene glycol, povidone, pregelatinized starch, and titanium dioxide. The total weight of the individual tablets is about 625 mg. FIG. 1A shows the XRPD pattern of the crushed and lightly ground tablets, while FIG. 1B shows the DSC of the crushed and lightly ground tablets. The XRPD pattern in FIG. 1A shows peaks attributable to Form I of fexofenadine hydrochloride, (as reported in Atwood, J. L.; Williams, M. D.; Garner, R. H.; Cone, E. J. Acta Cryst. 1974, B30, 2066) as well as a broad hump due to the excipients, with the broad microcrystalline cellulose peak in the 21-24° 2θ range. The DSC shows one peak at about 193° C., which corresponds to the melting point range of 193-199° C. for Form I fexofenadine hydrochloride. See Kumar, L.; Alam, M. S.; Meena, C. L.; Jain, R.; Bansal, A. K. Profiles Drug Subs. Excip. Rel. Methodology 2009, 34, 153.

Fexafenadine hydrochloride has a density of about 1.25 g/cm$^3$. The crushed and lightly ground tablets were treated successively with an iodobenzene/hexane solution of density ca. 1.36 g/cm$^3$, 1.32 g/cm$^3$, 1.32 g/cm$^3$, and 1.20 g/cm$^3$. The solution of density 1.36 g/cm$^3$ was prepared by mixing iodobenzene and hexane in the volume ratio of 1.5:1. Five mL of the solution was added to ca. 300 mg of the crushed tablets in 13/100 mm culture tube. The mixture was sonicated for 5 min with the use of Crest Tru-Sweep 275 HT sonicator. The culture tube with contents was then centrifuged until separation was effected, usually less than one minute. The floating white material (that of density less than 1.36 g/cm$^3$) was separated, placed in a culture tube, washed with an equal volume of hexane, and centrifuged. The white solid was separated from the liquid, treated with hexane, separated, and dried for 10 min in a vacuum chamber at room temperature and 50 Torr. The progress of the sequential density separations was monitored by XRPD of the dried powder. The more dense material from the sonication was discarded. The same procedure was followed for successive treatments of the previously density separated material with two solutions of density 1.32 g/cm$^3$. In the final density separation with the solution of density 1.20 g/cm$^3$, after the sonication and centrifugation, the more dense material was retained and the liquid above this material was discarded.

Figure 2A:
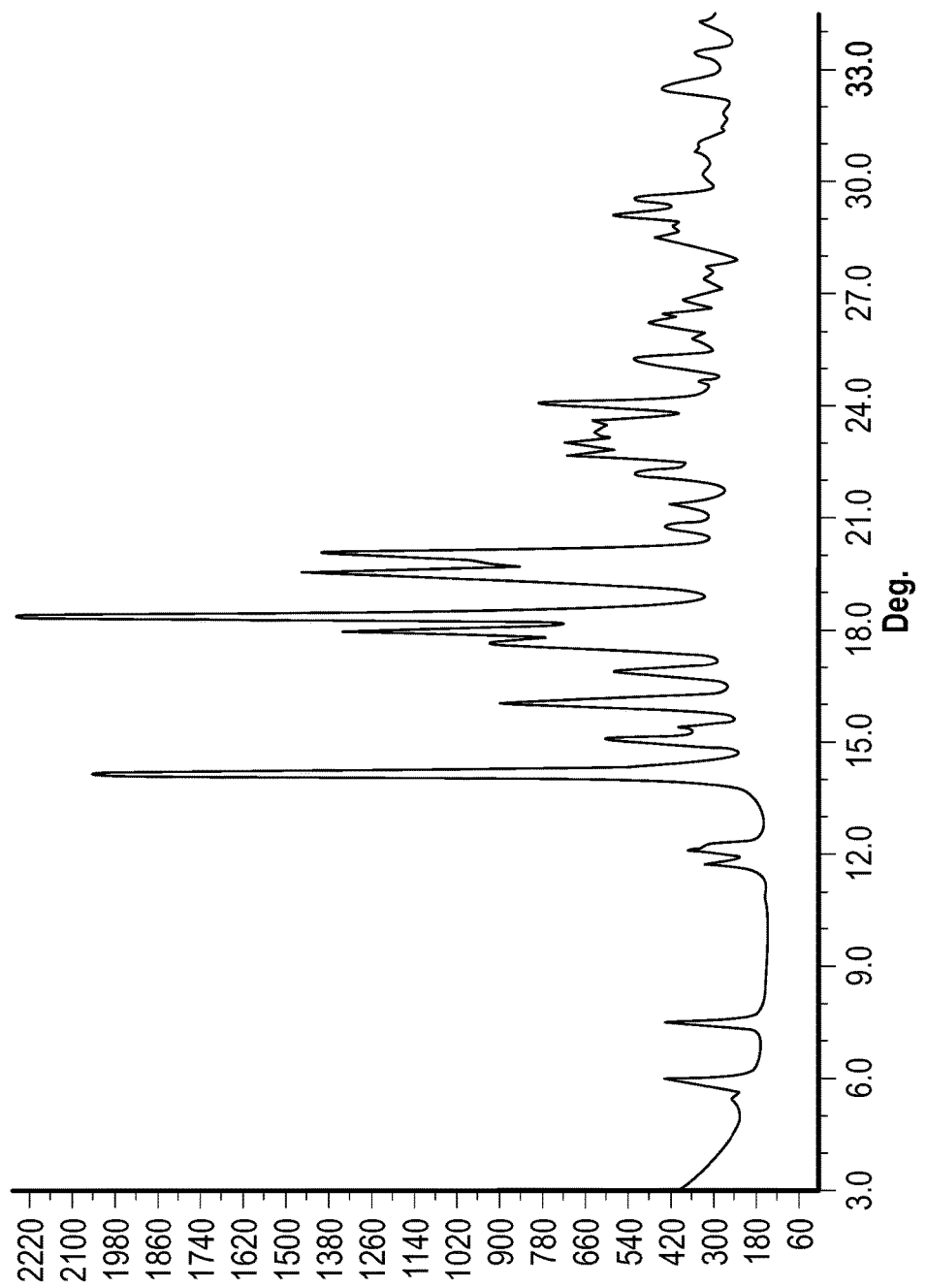
FIG. 2A shows the XRPD pattern of density separated fexofenadine hydrochloride.
Figure 2B:
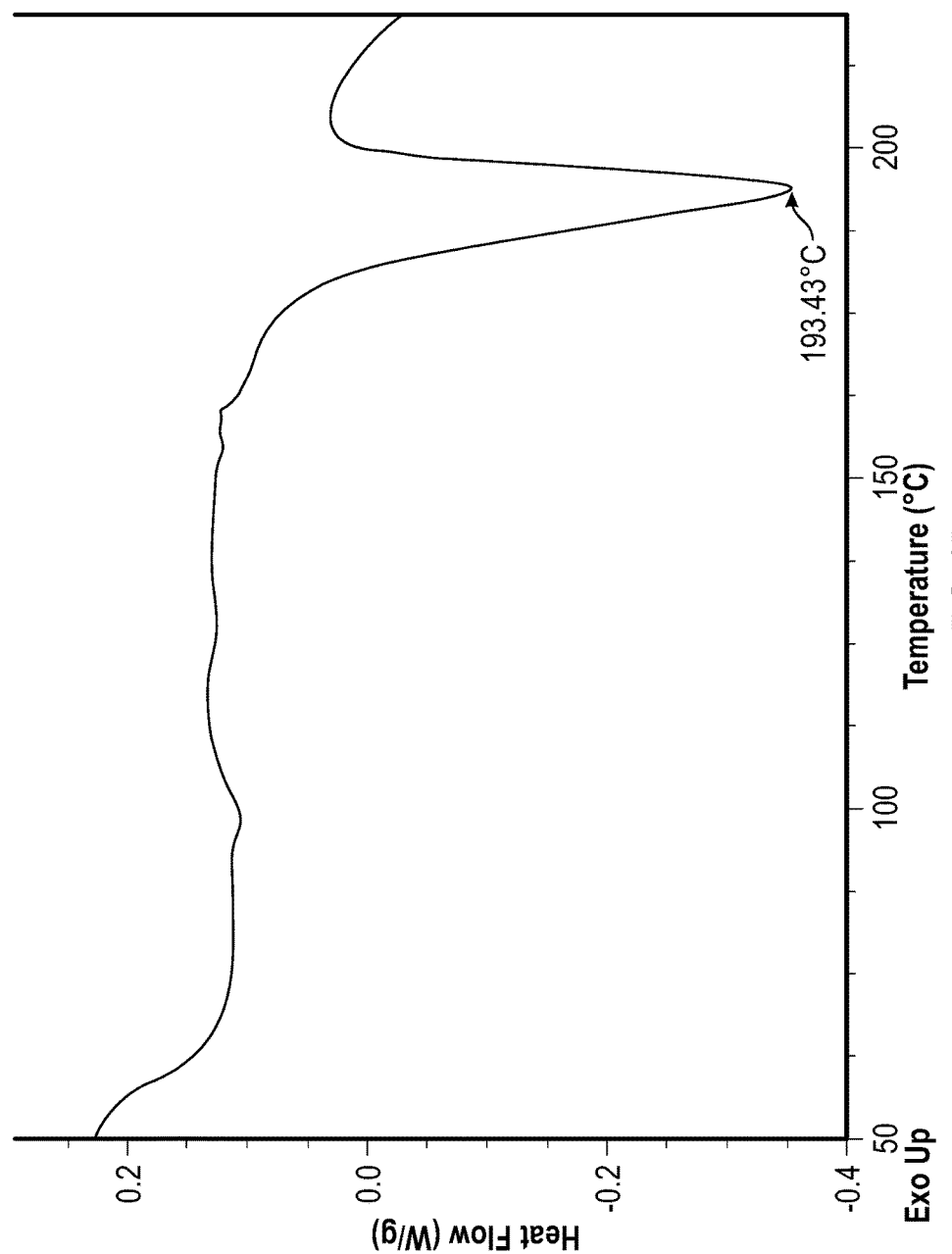
FIG. 2B shows the DSC thermogram of density separated fexofenadine hydrochloride.
Figure 3:
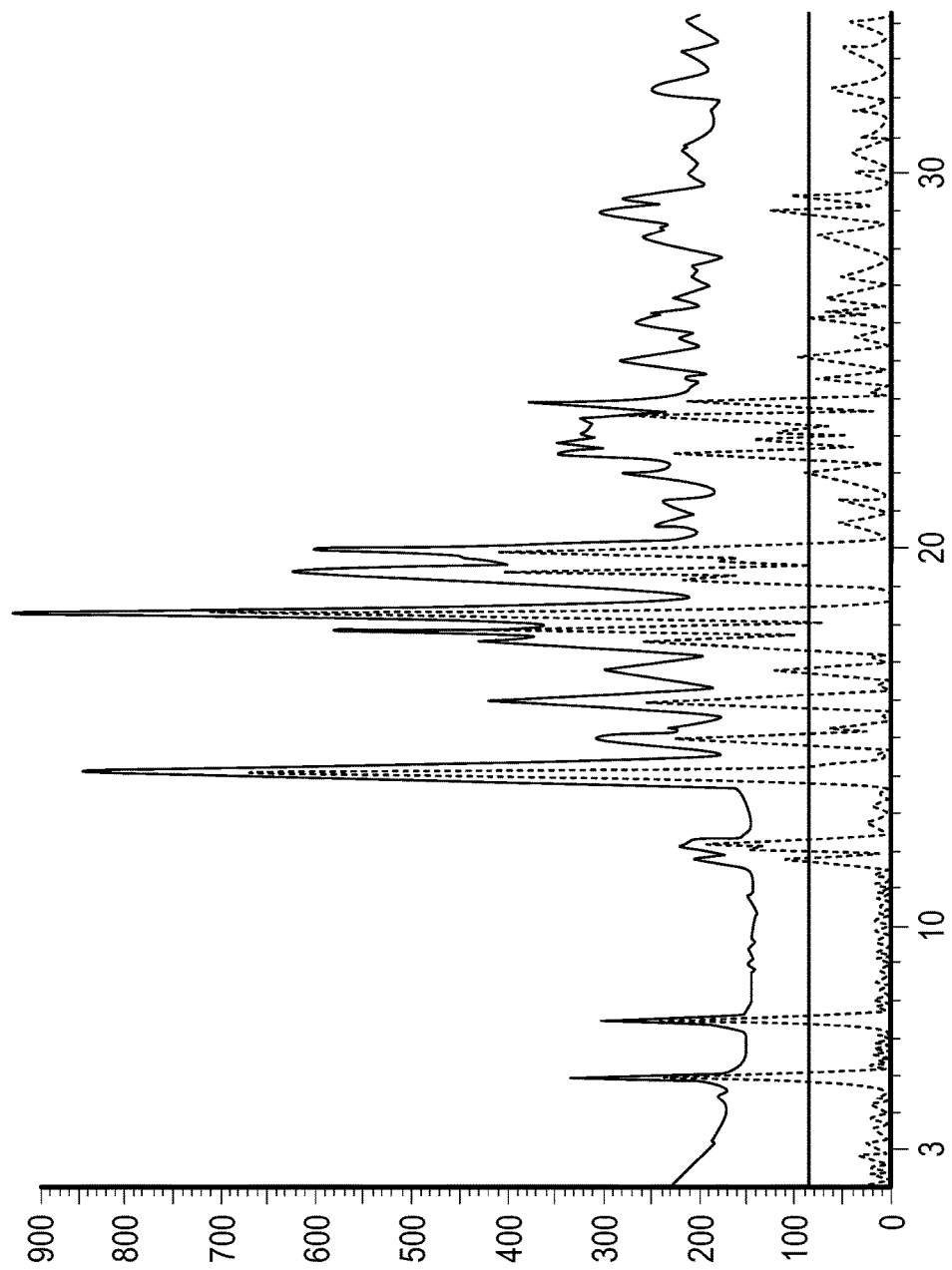
FIG. 3 illustrates the overlay of the XRPD pattern of density separated fexofenadine hydrochloride with the literature XRPD pattern of Form I fexofenadine hydrochloride.

The white crystalline material, which resulted from the density separation, produced the XRPD pattern and the DSC thermogram shown in FIGS. 2A and 2B, respectively. It may be seen that most of the excipients have been removed. Indeed, the XRPD pattern matches that of Form I of fexofenadine hydrochloride from the literature, FIG. 3, see Kumar, L.; Alam, M. S.; Meena, C. L.; Jain, R.; Bansal, A. K. Profiles Drug Subs. Excip. Rel. Methodology 2009, 34, 153. The DSC thermogram now shows a single peak for Form I fexofenadine hydrochloride at 194° C.

Example 2

Separation of Lansoprazole from Equate Lansoprazole Delayed Release Capsules, 15 mg.

Figure 4A:
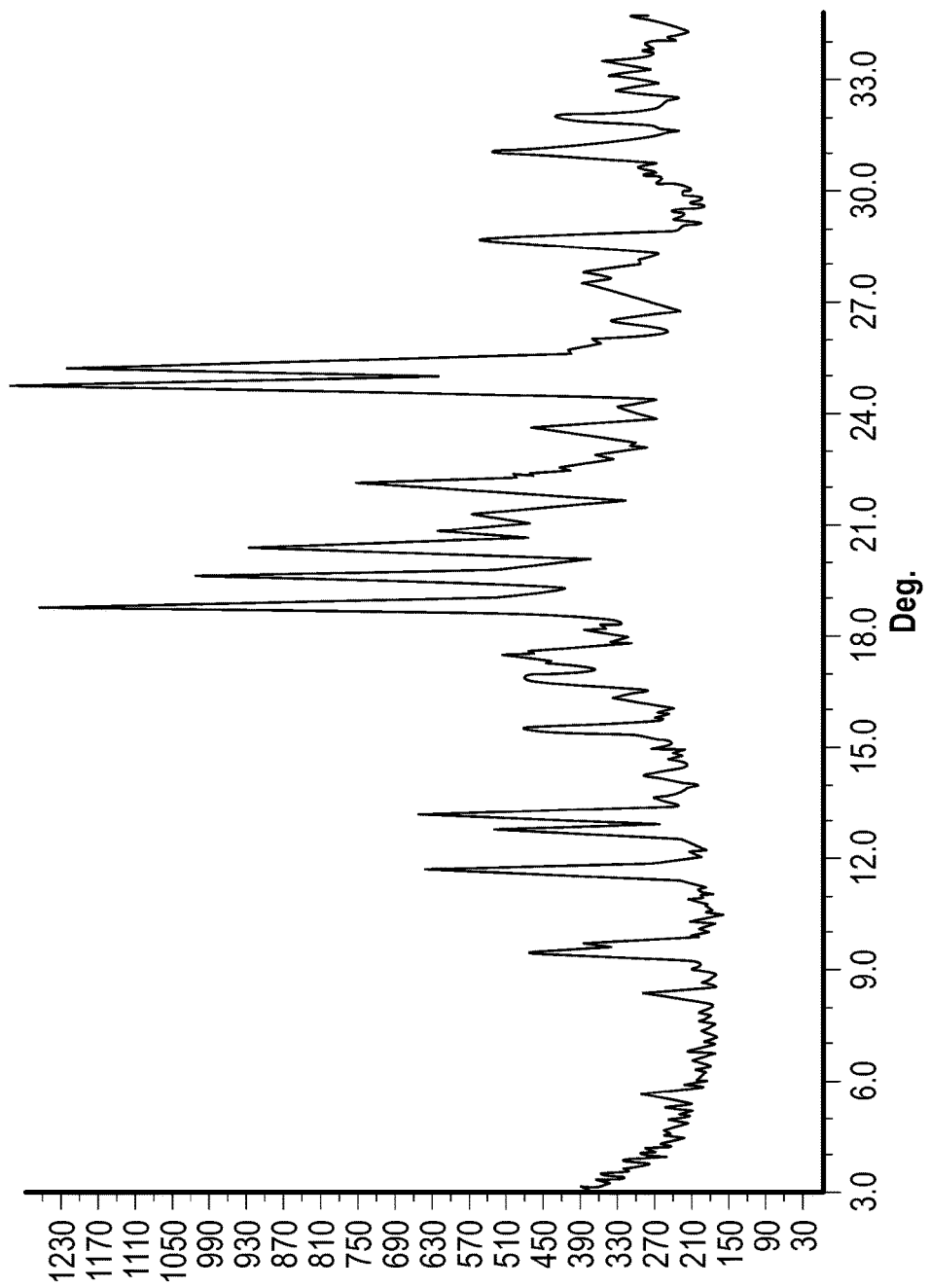
FIG. 4A shows the XRPD pattern of the crushed, ground, and powdered granules (Equate Lansoprazole Delayed Release Capsules).
Figure 4B:
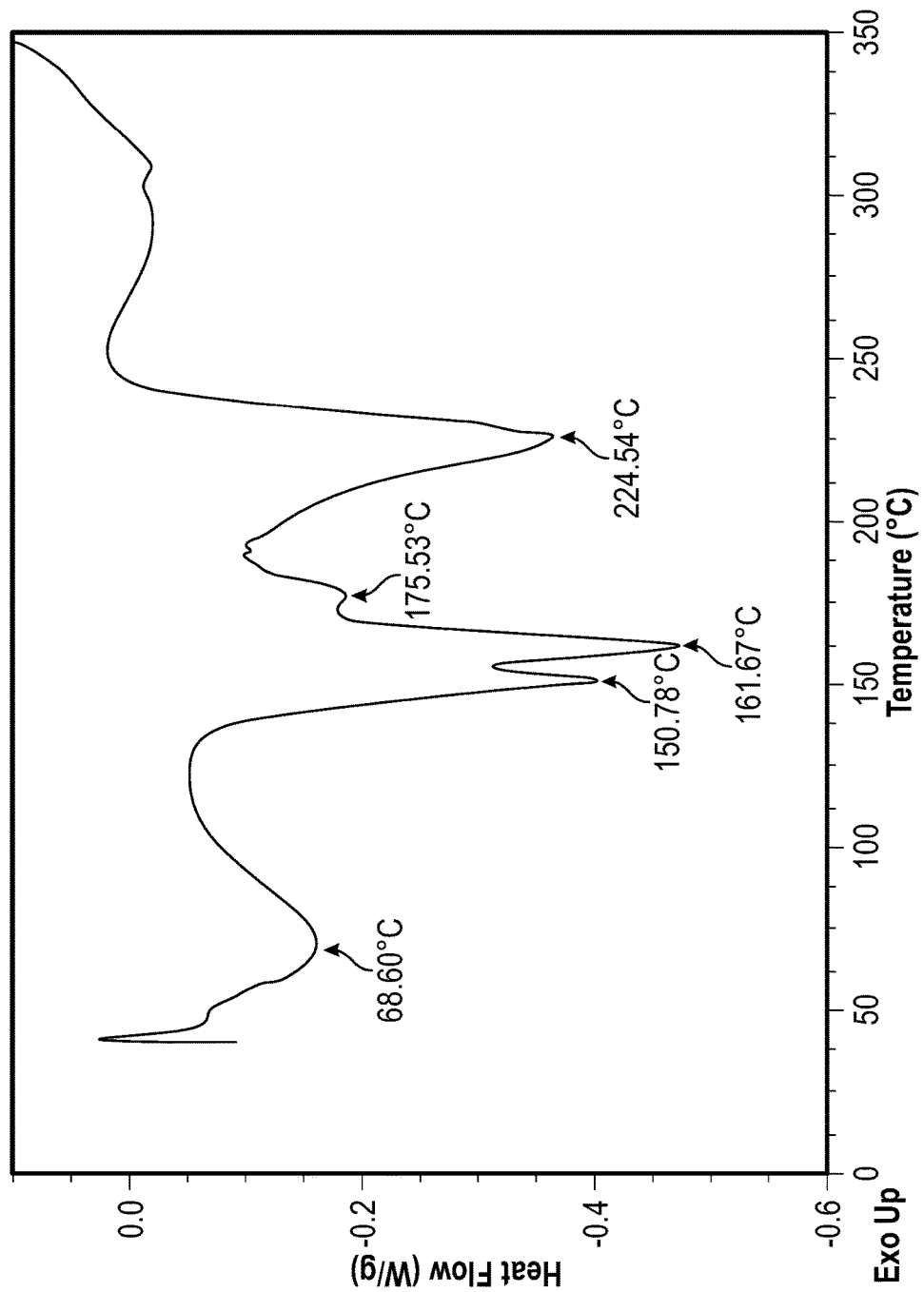
FIG. 4B shows the DSC thermogram of the crushed, ground, and powdered granules.

The commercial product Equate Lansoprazole Delayed Release Capsules, obtained from WalMart, according to the label consists of capsules containing 15 mg of lansoprazole with hypromellose, low substituted hydroxypropyl cellulose, mannitol, meglumine, methacrylic acid copolymer, polyethylene glycol, polysorbate 80, sodium lauryl sulfate, sugar spheres, talc, and titanium dioxide. The total weight of the contents of the individual capsules (in the form of granules) was about 170 mg. FIG. 4A shows the XRPD pattern of the crushed, ground, and powdered granules while FIG. 4B shows the DSC of the crushed, ground, and powdered granules. The XRPD pattern in FIG. 4A shows a few peaks which may be attributable to Form I of lansoprazole, see Tian, J.; Dalgarno, S. J.; Atwood, J. L. J. Am. Chem. Soc. 2011, 133, 1399, as well as peaks attributable to other crystalline compounds. Additionally, there is also an amorphous hump in the 12-26° 2θ range. The DSC shows at least four peaks, in addition to the broad feature centered at about 70° C.

Lansoprazole has a density of about 1.5 g/cm$^3$. The crushed, ground, and powdered granules were treated successively with an iodobenzene/hexane solution of density ca. 1.52 g/cm$^3$, 1.46 g/cm$^3$, 1.51 g/cm$^3$, 1.47 g/cm$^3$, 1.50 g/cm$^3$, and 1.50 g/cm$^3$. The solution of density 1.52 g/cm$^3$ was prepared by mixing iodobenzene and hexane in the volume ratio of 2.8:1. Five mL of the solution was added to ca. 300 mg of the crushed, ground, and powdered granules in 13/100 mm culture tube. The mixture was sonicated for 5 min with the use of Crest Tru-Sweep 275 HT sonicator, The culture tube with contents was then centrifuged. The floating white (the material of density less than 1.52 g/cm$^3$) was separated, placed in a culture tube, washed with an equal volume of hexane, and centrifuged. The white solid was separated from the liquid, treated with hexane, separated, and dried for 10 min in a vacuum chamber at room temperature and 50 Torr. The progress of the sequential density separations was monitored by XRPD of the dried powder. The more dense material from the sonication was discarded. The same procedure was followed for the treatment of the previously density separated material with solution of density 1.46 g/cm$^3$. Here, the more dense material was retained and the liquid and floating solids above this material were discarded. The successive density separation treatments were carried out as described above.

Figure 5A:
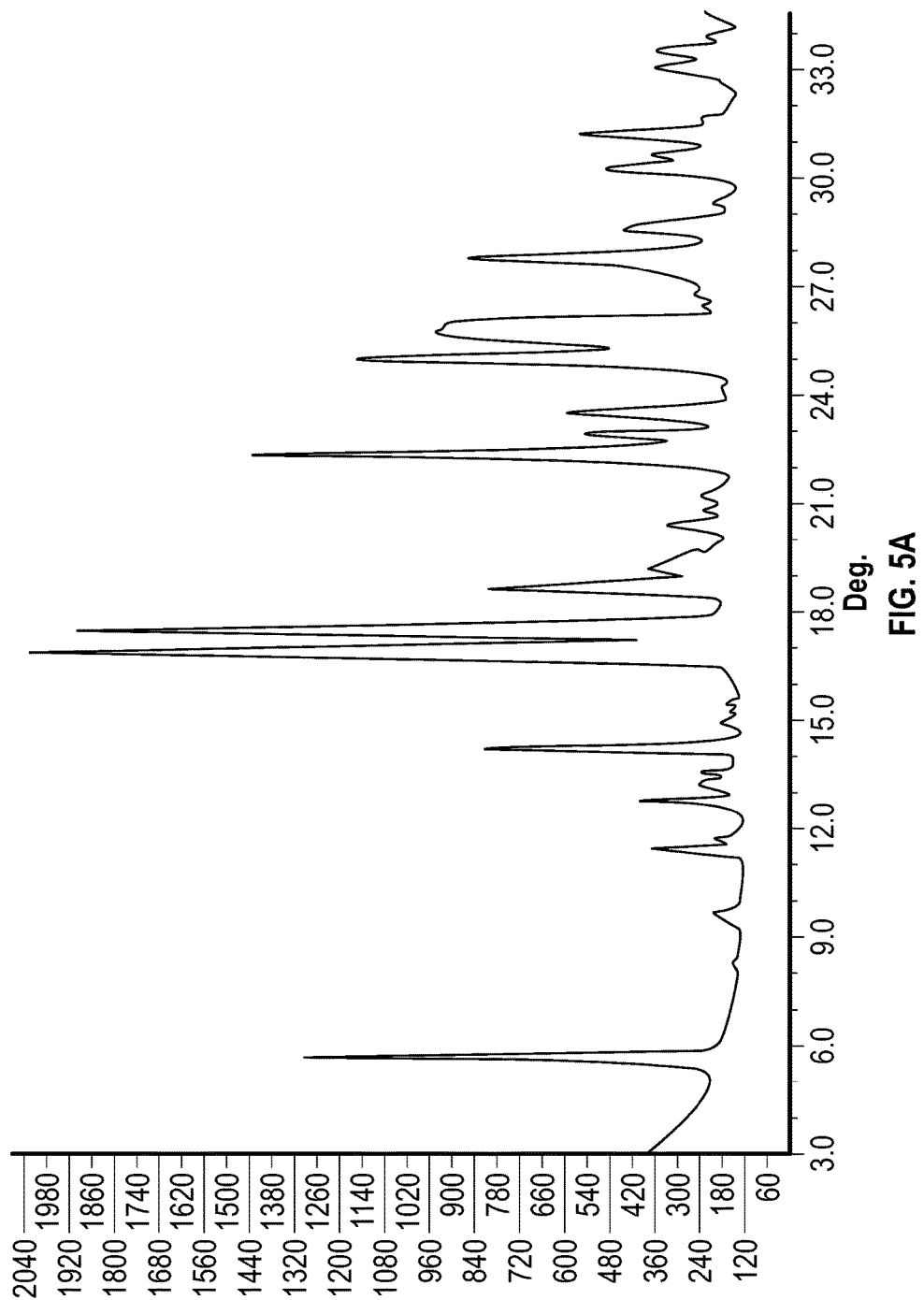
FIG. 5A shows the XRPD pattern of density separated lansoprazole.
Figure 5B:
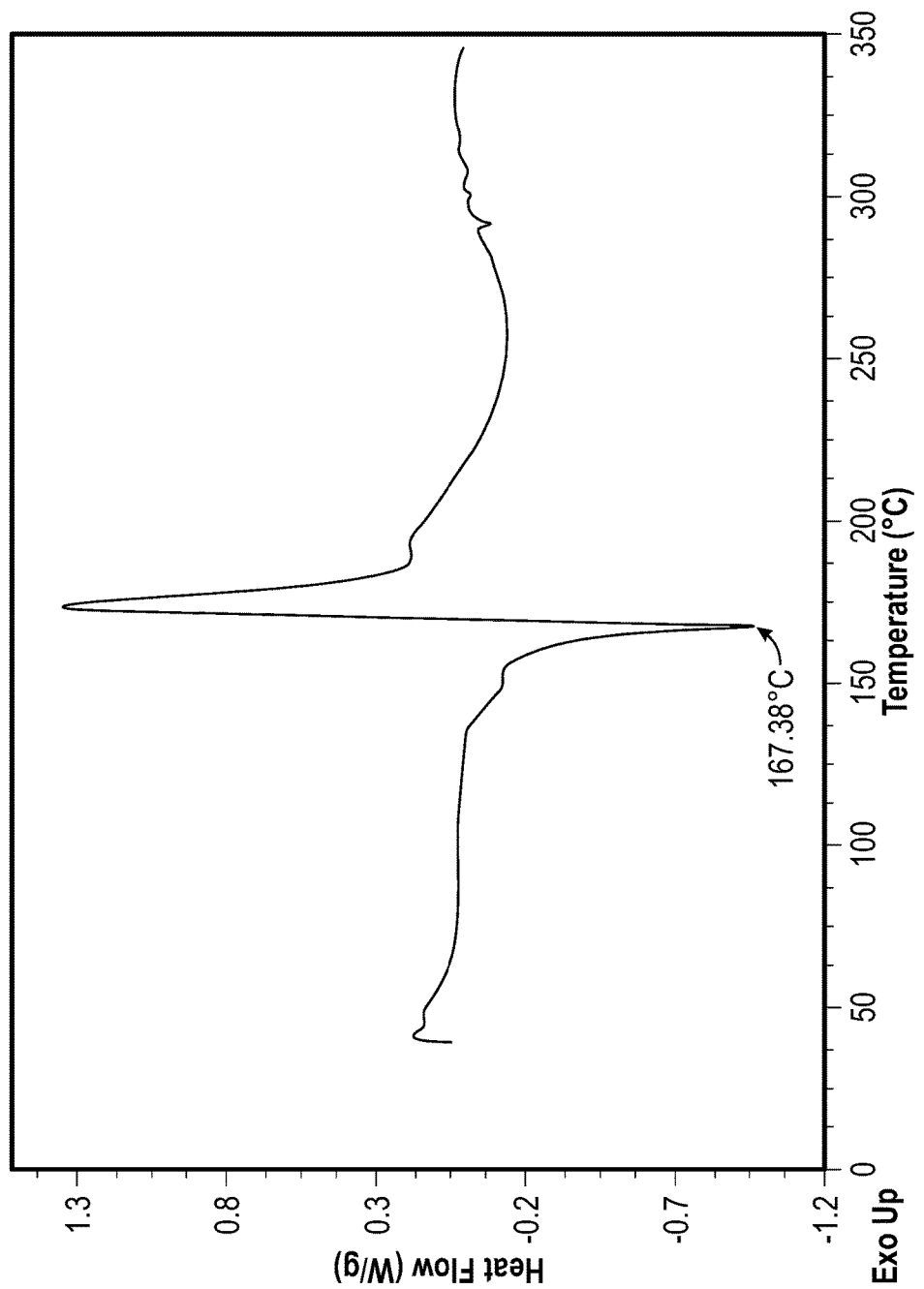
FIG. 5B shows the DSC thermogram of density separated lansoprazole.
Figure 6:
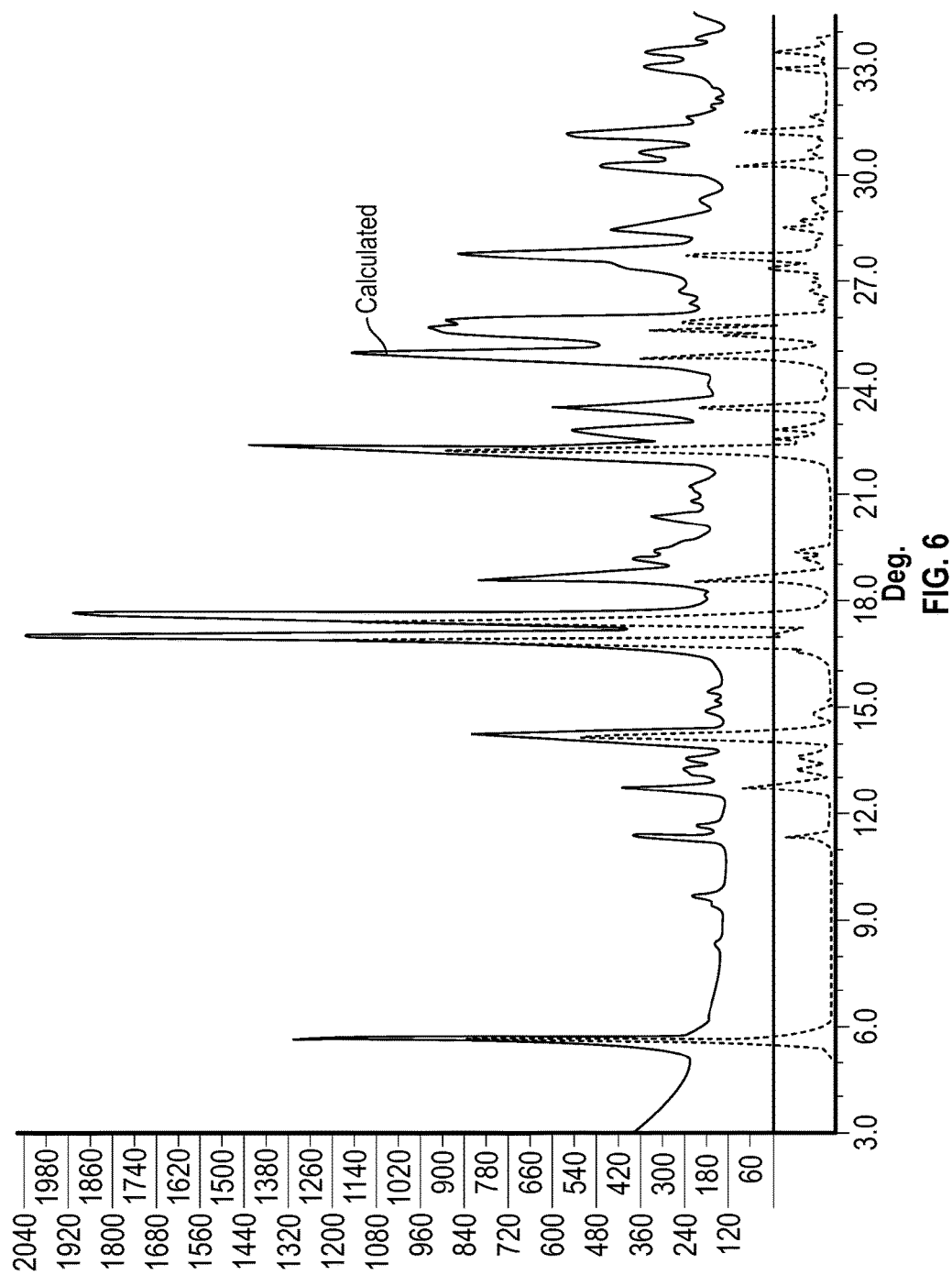
FIG. 6 illustrates the overlay of the XRPD pattern of density separated lansoprazole with the calculated literature XRPD pattern of Form I lansoprazole.

The white crystalline material, which resulted from the sixth density separation, produced the XRPD pattern and the DSC thermogram shown in FIGS. 5A and 5B, respectively. It may be seen that most of the excipients have been removed. Indeed, the XRPD pattern matches that of Form I of lansoprazole from the literature, FIG. 6.6. The DSC thermogram now shows a single peak for Form I lansoprazole at 167° C.

The description herein is merely exemplary in nature and, thus, variations that do not depart from the gist of that which is described are intended to be within the scope of the teachings. Such variations are not to be regarded as a departure from the spirit and scope of the teachings.

I claim:

1. A method of physically separating an active pharmaceutical ingredient (API) from a pharmaceutical formulation comprising an API and excipients, the method comprising:
providing the pharmaceutical formulation in powdered form, the powdered form comprising a mixture of API particulates and excipient particulates;
generating a first liquid separation medium having a selected density greater than the density of the API particulates and less than the density of at least a portion of the excipient particulates;

introducing the particulates to a vessel containing the first liquid separation medium;

centrifuging the vessel containing the first liquid separation medium and the particulates so that the particulates having a density less than the density of the first liquid separation medium are floated to form a first floated fraction and the particulates having a density greater than the first liquid separation medium forms a first pellet fraction at the bottom of the vessel, the first floated fraction comprising at least a portion of the API particulates; and removal of the first floated fraction comprising at least a portion of the API particulates;

wherein the API particulates are insoluble in the first liquid separation media and wherein the API particles have a density of between about 1.1 g/cm$^3$ to about 1.5 g/cm$^3$.

2. The method according to claim 1, further comprising:

generating a second liquid separation medium have a selected density less than the density of the API particulates and greater than the density of at least a portion of the excipient particulates;

introducing the first floated fraction to a vessel containing the second liquid separation medium;

centrifuging the vessel containing the second liquid separation medium and the first floated fraction so that the particulates having a density less than the density of the second liquid separation medium are floated to form a second floated fraction and the particulates having a density greater than the second liquid separation medium forms a second pellet fraction at the bottom of the vessel, the second pellet fraction comprising at least a portion of the API particulates; and removal of the second pellet fraction comprising at least a portion of the API particulates;

wherein the API particulates are insoluble in the second liquid separation media.

3. The method according to claim 2, wherein generating the first or second liquid separation media comprises mixing two miscible liquids having different densities to produce the first or second liquid separation media having the selected density.

4. The method according to claim 3, wherein the two miscible liquids comprises a first more dense liquid and a second less dense liquid, the first more dense liquid having a density between about 1.6 g/cm$^3$ to about 2.0 g/cm$^3$ and the second less dense liquid having a density between about 0.6 g/cm$^3$ to about 0.9 g/cm$^3$.

5. The method according to claim 4, wherein the first more dense liquid is selected from the group consisting of iodobenzene, bromopropane, bromobutane, 1,4-dibromobenzene, and 1,3-dibromobenzene, and wherein the second less dense liquid is selected from the group consisting of hexane, cyclohexane, toluene, o-xylene, pentane, and heptane.

6. The method according to claim 3, wherein the two miscible liquids comprise a halocarbon and a hydrocarbon.

7. The method according to claim 3, wherein the two miscible liquids are selected from the group consisting of iodobenzene, bromopropane, bromobutane, 1,4-dibromobenzene, 1,3-dibromobenzene, hexane, cyclohexane, toluene, o-xylene, pentane, and heptane.

8. The method according to claim 2, wherein generating the first or second liquid separation media comprises dissolving a solute in water to produce the first or second liquid separation media having the selected density.

9. The method according to claim 3, wherein the two miscible liquids are aqueous solutions having different concentrations of solute.

10. The method according to claim 9, wherein the solute is a salt.

11. The method according to claim 10, wherein the salt is selected from the group consisting of CsCl, KBr, CsBr, CsI, RbCl, RbBr, RbI, and KI.

12. The method according to claim 3, wherein the solid form of the API does not change during the method as determined by XRPD.

13. The method according to claim 3, wherein the selected density of the first liquid separation medium and the second liquid separation medium is between about 1.1 g/cm$^3$ to about 1.5 g/cm$^3$.

14. The method according to claim 3, wherein the density of the API particulates is between about 1.2 g/cm$^3$ to about 1.4 g/cm$^3$.

15. The method according to claim 3, wherein the density of the excipient particulates is less than about 1.1 g/cm$^3$ or greater than about 1.5 g/cm$^3$.

16. The method according to claim 3, further comprising applying mechanical energy to the pharmaceutical formulation with sufficient force and duration to generate a powdered form of the pharmaceutical formulation.

17. The method according to claim 3, wherein the second pellet fraction comprises API characterized by a purity of between about 85% to about 99% by weight.

18. The method according to claim 3, further comprising performing sonication on the vessel containing the first or second liquid separation media and the particulates with sufficient force and duration to free the API particulates from the excipient particulates.

19. The method according to claim 3, wherein the pharmaceutical formulation is selected from the group consisting of those having the brand name Lipitor, Plavix, Nexium, Abilify, Seroquel, Januvia, Reyataz, Niaspan, Vyvanse, Venlafaxine, Zyvox, Treanda, Exelon, Atorvastatin, Onglyza, Norvir, Revlimid, Tarceva, Pristiq, Celebrex, Lyrica, Crestor, Actos, Cymbalta, Oxycontin, Lexapro, Cialis, Levaquin, Dexilant, Aloxi, Invega, Valcyte, Avelox, and Chantix.

* * * * *